(12) United States Patent
Kojima et al.

(10) Patent No.: US 8,226,567 B2
(45) Date of Patent: Jul. 24, 2012

(54) BLOOD PRESSURE MANOMETER

(75) Inventors: Takeshi Kojima, Hikone (JP); Tsuyoshi Yuasa, Hikone (JP); Shinichi Fumuro, Hikone (JP); Yoshitoshi Kanetsuna, Hikone (JP)

(73) Assignee: Panasonic Corporation, Osaka (JP)

( * ) Notice: Subject to any disclaimer, the term of this patent is extended or adjusted under 35 U.S.C. 154(b) by 241 days.

(21) Appl. No.: 11/956,279

(22) Filed: Dec. 13, 2007

(65) Prior Publication Data

US 2008/0146949 A1    Jun. 19, 2008

(30) Foreign Application Priority Data

Dec. 14, 2006    (JP) .................................. 2006-337377

(51) Int. Cl.
*A61B 5/02*    (2006.01)
(52) U.S. Cl. ....................................... 600/490; 600/485
(58) Field of Classification Search .................. 600/481, 600/483, 485, 490–503, 476–480, 310, 595
See application file for complete search history.

(56) References Cited

U.S. PATENT DOCUMENTS

| | | | |
|---|---|---|---|
| 6,211,787 B1 * | 4/2001 | Yoshiike et al. ........... 340/573.1 |
| 6,344,025 B1 | 2/2002 | Inagaki et al. |
| 7,419,471 B2 * | 9/2008 | Sasagawa et al. ............. 600/490 |
| 7,468,034 B2 * | 12/2008 | Ouchi ........................... 600/481 |
| 2002/0087054 A1 | 7/2002 | Lin et al. |
| 2004/0210155 A1 * | 10/2004 | Takemura et al. ............. 600/534 |
| 2005/0187484 A1 | 8/2005 | Sano et al. |
| 2005/0215910 A1 * | 9/2005 | Yang et al. .................... 600/474 |
| 2006/0058591 A1 | 3/2006 | Garboski et al. |
| 2006/0111639 A1 | 5/2006 | Su |
| 2006/0217612 A1 * | 9/2006 | Ouchi .......................... 600/407 |
| 2007/0038128 A1 * | 2/2007 | Sawanoi et al. ............... 600/485 |
| 2007/0167845 A1 | 7/2007 | Sasagawa et al. |

FOREIGN PATENT DOCUMENTS

| | | | |
|---|---|---|---|
| JP | 01121996 A | * | 5/1989 |
| JP | 05-056938 A | | 3/1993 |
| JP | 2005-237560 A | | 9/2005 |
| JP | 2006-204543 A | | 8/2006 |
| WO | WO-2005/074793 A1 | | 8/2005 |

OTHER PUBLICATIONS

English Translated JP 01121996 A.*
European Search Report for the Application No. EP 07 02 3174 dated Aug. 8, 2008.

* cited by examiner

*Primary Examiner* — Navin Natnithithadha
(74) *Attorney, Agent, or Firm* — Cheng Law Group, PLLC

(57) ABSTRACT

A blood pressure manometer comprises a body and a separate display, and the body and separate display are provided with first and second communication parts, respectively. The first communication part has a light emitting element and is configured so that the element sends an infrared signal including blood pressure data. The second communication part has a light receiving element and is configured so that the light receiving element receives the infrared signal including the blood pressure data from the first communication part. The light emitting element is supported by the body to be opposite a subject even if a blood pressure measuring portion of the body measures the subject's blood pressure from any of the subject's left and right regions. The light receiving element is supported by the separate display to received the infrared signal which is sent from the light emitting element to be reflected on the subject.

10 Claims, 14 Drawing Sheets

FIG. 7A
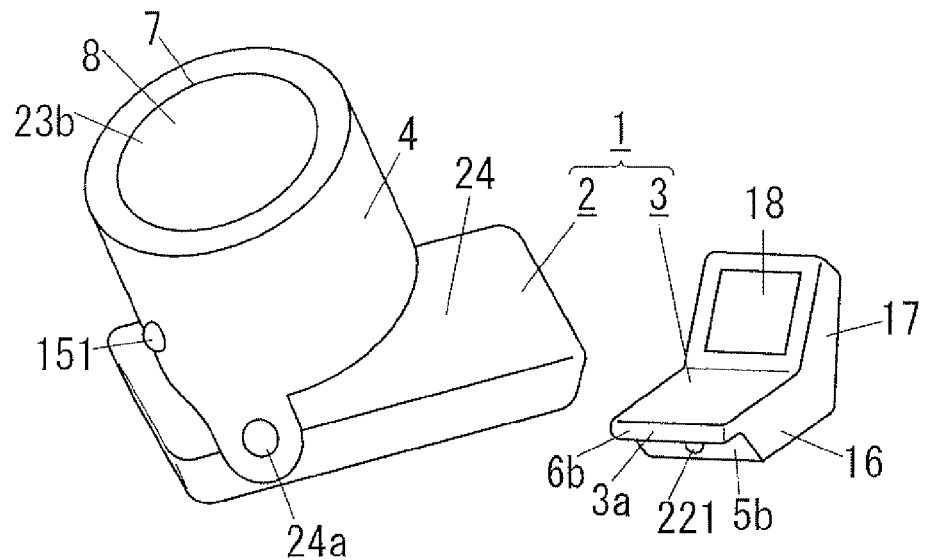
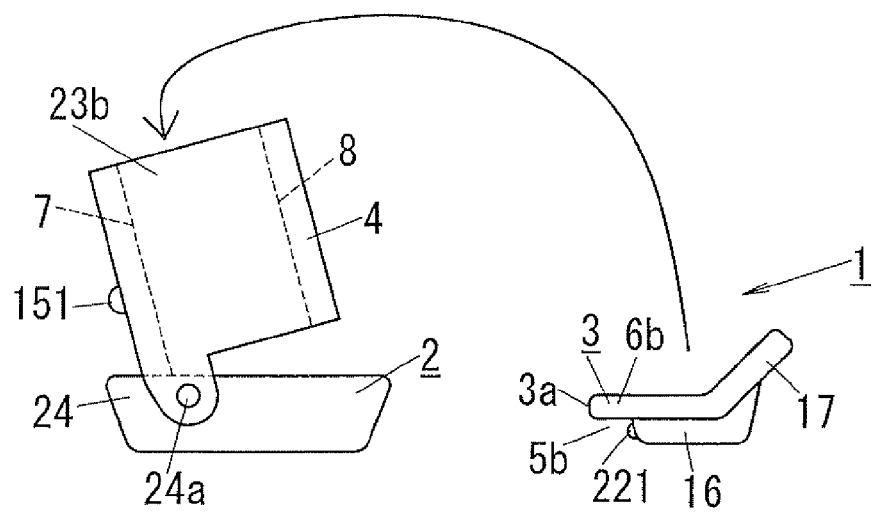
FIG. 7B
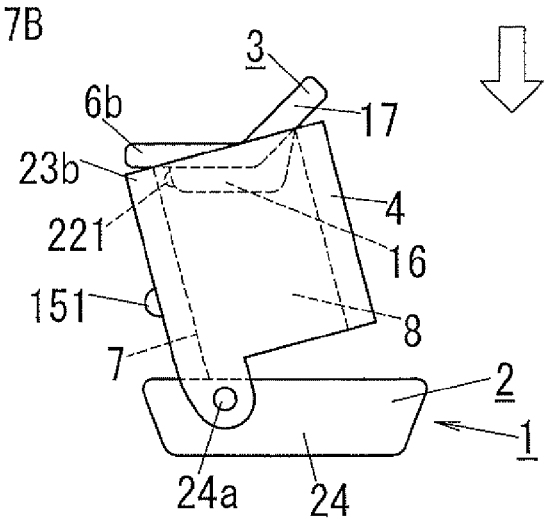

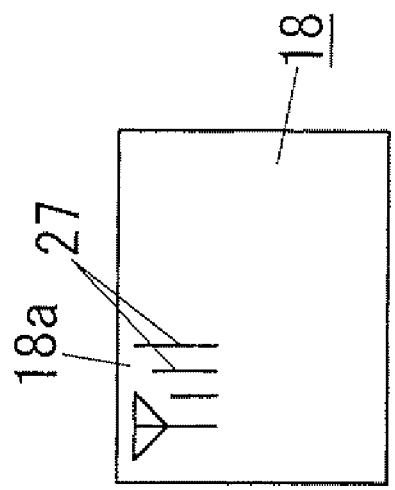
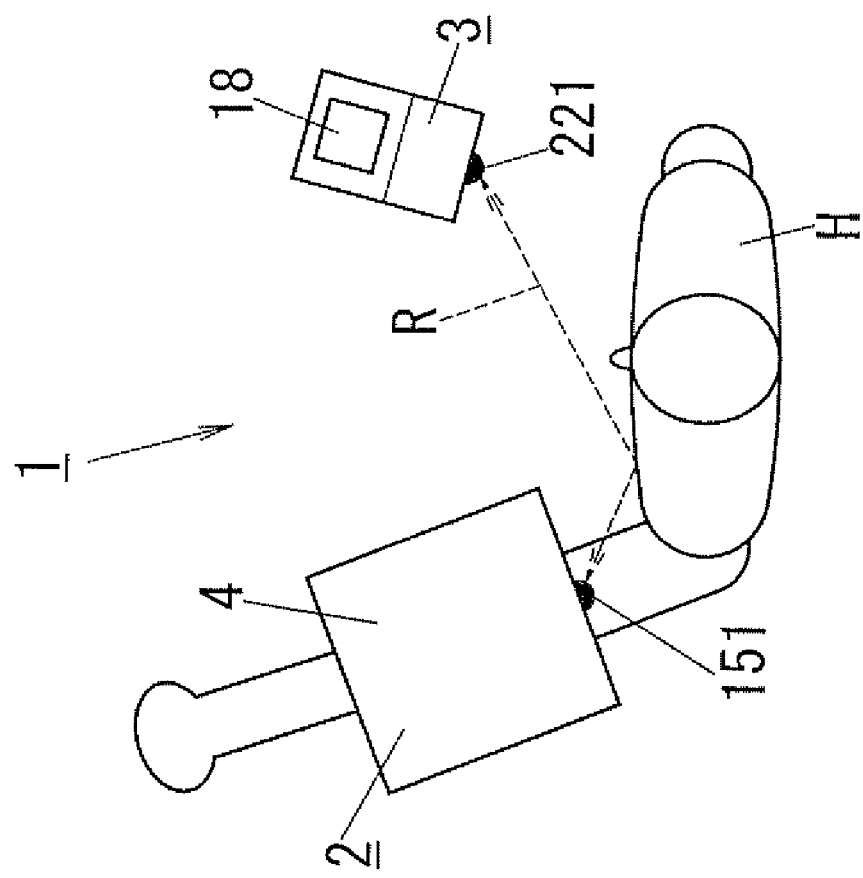
FIG. 12A
FIG. 12B

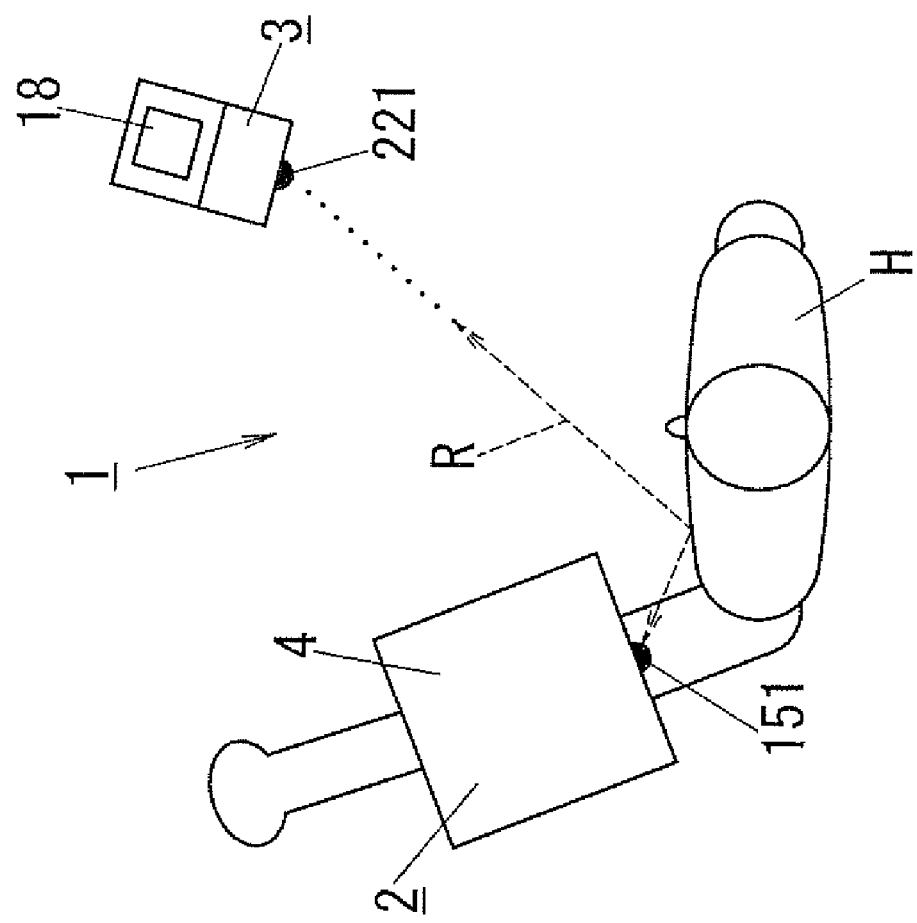
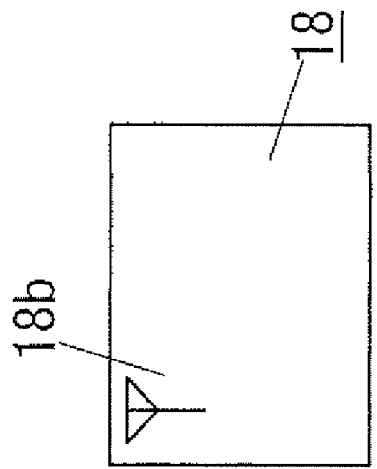

BLOOD PRESSURE MANOMETER

TECHNICAL FIELD

The invention relates to blood pressure manometers.

BACKGROUND ART

A blood pressure manometer comprising a body and a separate display has been already known (Japanese Patent Application Publication Nos. 2005-237560, 2006-204543 and H5-56938). For example, the body comprises a blood pressure measuring portion and a first communication part, and the separate display comprises a second communication part and a display part. The blood pressure measuring portion is configured to measure a subject's blood pressure from a predetermined region to obtain blood pressure data. The first communication part is configured to send, for example, an infrared signal including the blood pressure data. The second communication part is configured to receive the infrared signal including the blood pressure data from the first communication part. The display part is configured to display the subject's blood pressure based on the blood pressure data included in the infrared signal.

In such blood pressure manometer, when subject's blood pressure is measured, the separate display can be located so that the subject can easily see the display, and accordingly the blood pressure can be measured in correct posture. Also, in case that a subject needs to show the blood data measured at home to a doctor, the carrying of the separate display is only required, and therefore the blood pressure manometer is convenient for the subject. However, in case that the communication between the first and second communication parts is infrared communication, good communication is not always performed. Also, in order to secure good infrared communication, there is an issue that configuration of a blood pressure manometer is complicated.

The infrared communication can be classified into a direct type and a reflection type. Specifically, the direct type is used for e.g. a TV set and a remote control, and an infrared signal sent from the remote control is directly received by a light receiving element in the TV set. The reflection type is used for e.g. an installation type Alkali-Ion-Water electrolyzer and a remote control. This remote control is installed at a water tap in a kitchen or the like, and the electrolyzer is installed near the remote control. The remote control sends an infrared signal toward a ceiling, and the electrolyzer receives the infrared signal reflected on the ceiling.

Herein, as shown in FIGS. 15A and 15B, in case that direct type infrared communication is used for first and second communication parts in a blood pressure manometer A1 comprising a body A2 and a separate display A3, it must be considered that a subject's blood pressure is measured from either of the subject's left and right regions. A blood pressure measuring portion A4 of the body A2 measures the blood pressure of the subject (H) from either of the subject's left and right arms. In this case, the separate display A3 is located so that the subject (H) can easily see a display part A18 of the separate display A3. Because of this, the first communication part must be provided with a pair of light emitting elements A151 located at the left and right sides of the body A2, and the second communication part must be also provided with a pair of light receiving elements A221 located at the left and right sides of the separate display A3. In this configuration, the blood pressure manometer A1 not only remarkably rises in production cost but also can be hardly downsized. In FIGS. 15A and 15B, R depicts an infrared signal.

In case that reflection type infrared communication is used for the first and second communication parts, an infrared signal sent from the first communication part needs to be reflected on, for example, a ceiling or a wall. When the infrared signal is reflected on a ceiling, the blood pressure manometer A1 easily causes malfunction by noise from fluorescent lamps. In order to remove the noise, if the second communication part is mounted with an expensive filter having a high filtering effect, the production cost increases. When the infrared signal is reflected on a left or right wall etc., good infrared communication can be hardly achieved in case that an obstacle exists between the blood pressure manometer A1 and the wall. That is, working conditions are restricted, so that the blood pressure manometer A1 becomes very user-unfriendly.

DISCLOSURE OF THE INVENTION

It is an object of the present invention to avoid an increase in the number of elements of first and second communication parts to realize downsizing and cost reduction, without restricting working conditions while making it possible to measure a subject's blood pressure from any of the subject's left and right regions.

A blood pressure manometer of the present invention comprises a blood pressure measuring portion, a first communication part, a body, a second communication part, a display part and a separate display. The blood pressure measuring portion is configured to measure a subject's blood pressure from either of the subject's left and right regions to obtain blood pressure data. The first communication part has a light emitting element and is configured so that the light emitting element sends an infrared signal including the blood pressure data. The body comprises the blood pressure measuring portion and the first communication part. The second communication part has a light receiving element and is configured so that the light receiving element receives the infrared signal including the blood pressure data from the first communication part. The display part is configured to display the subject's blood pressure based on the blood pressure data included in the infrared signal received by the light receiving element. The separate display is separated from the body and comprises the second communication part and the display part. In an aspect of the invention, the light emitting element is supported by the body to be opposite the subject even if the blood pressure measuring portion measures the subject's blood pressure from any of the subject's left and right regions. In addition, the light receiving element is supported by the separate display to received the infrared signal which is sent from the light emitting element to be reflected on the subject. Herein, since the subject exists near the body and the separate display in general, existence of an obstacle(s) between the subject and the blood pressure manometer can be eliminated. Moreover, in order to make the infrared signal from the first communication part to the second communication part reflect on the subject, the first and second communication parts do not need to be provided with a plural of light emitting elements and a plural of light receiving elements, respectively. Accordingly, it is possible to avoid an increase in the number of elements of the first and second communication parts to realize downsizing and cost reduction, without restricting working conditions while making it possible to measure a subject's blood pressure from any of the subject's left and right regions.

In an embodiment, the blood pressure measuring portion includes a cuff into which either of the subject's left and right arms is inserted and is configured to measure the subject's blood pressure through the cuff to obtain blood pressure data. In addition, the light receiving element is supported by the separate display to be opposite the subject when the display part is opposite the subject.

In an embodiment, the front of the body is formed with a protuberance and a recess arranged up and down, respectively. The protuberance includes the cuff, and the recess includes the light emitting element. The front side of the separate display is also formed with an eaves and a recess arranged up and down, respectively. The recess includes the light receiving element. In this case, it is possible to prevent the subject from covering the light emitting element and light receiving element by mistake. The protuberance and eaves can block noise from fluorescent lamps to the light emitting element and light receiving element, and accordingly malfunction by the noise can be prevented.

In an embodiment, the separate display can be attached to and detached from the body, and the body further comprises an interruption means. The interruption means interrupts the communication pass between the first and second communication parts when the separate display is attached to the body. In this embodiment, when the separate display is attached to the body, namely when the blood pressure manometer is not used, it is possible to prevent malfunction by unwanted communication between the first and second communication parts.

In an embodiment, the separate display can be attached to and detached from the body, and the body further comprises a switch. The switch turns on at least the first communication part when the separate display is detached from the body, and also turns off at least the first communication part when the separate display is attached to the body. In another embodiment, the separate display can be attached to and detached from the body, and the separate display further comprises a switch that turns on at least the second communication part when the separate display is detached from the body and also turns off at least the second communication part when the separate display is attached to the body. In these embodiments, when the separate display is attached to the body, namely when the blood pressure manometer is not used, it is possible to prevent malfunction by unwanted communication between the first and second communication parts. Moreover, when the first or second communication part is turned off, the first or second communication part does not consume electric power and accordingly power saving can be achieved.

In an embodiment, the body further comprises a human body sensor and a controller. The human body sensor is configured to detect whether or not a human body exists in a target space. The controller is configured to stop operation of the blood pressure measuring portion when the human body sensor detects that a human body does not exist in the target space. In this case, it is possible to prevent unwanted operation of the blood pressure measuring portion when a subject does not exist in the target space.

In an embodiment, the separate display further comprises a notice means configured to notify the subject of strength of the infrared signal received by the light receiving element. In this embodiment, the separate display can be prevented from being moved too far from the body, and good infrared communication between the first and second communication parts can be secured. Consequently, a measurement error can be avoided. Loss of the separate display can be also prevented.

BRIEF DESCRIPTION OF THE DRAWINGS

Preferred embodiments of the invention will now be described in further details. Other features and advantages of the present invention will become better understood with regard to the following detailed description and accompanying drawings where:

FIG. 7A is a schematic diagram of a blood pressure manometer in accordance with an embodiment of the present invention, and FIG. 7B is an explanatory diagram of attachment of a separate display to a body;

FIGS. 12A and 12B are explanatory diagrams of operation in case of good infrared communication of a blood pressure manometer in accordance with an embodiment of the present invention;

FIGS. 13A and 13B are explanatory diagrams of operation in case of no good infrared communication of the blood pressure manometer;

BEST MODE FOR CARRYING OUT THE INVENTION

Figure 1:
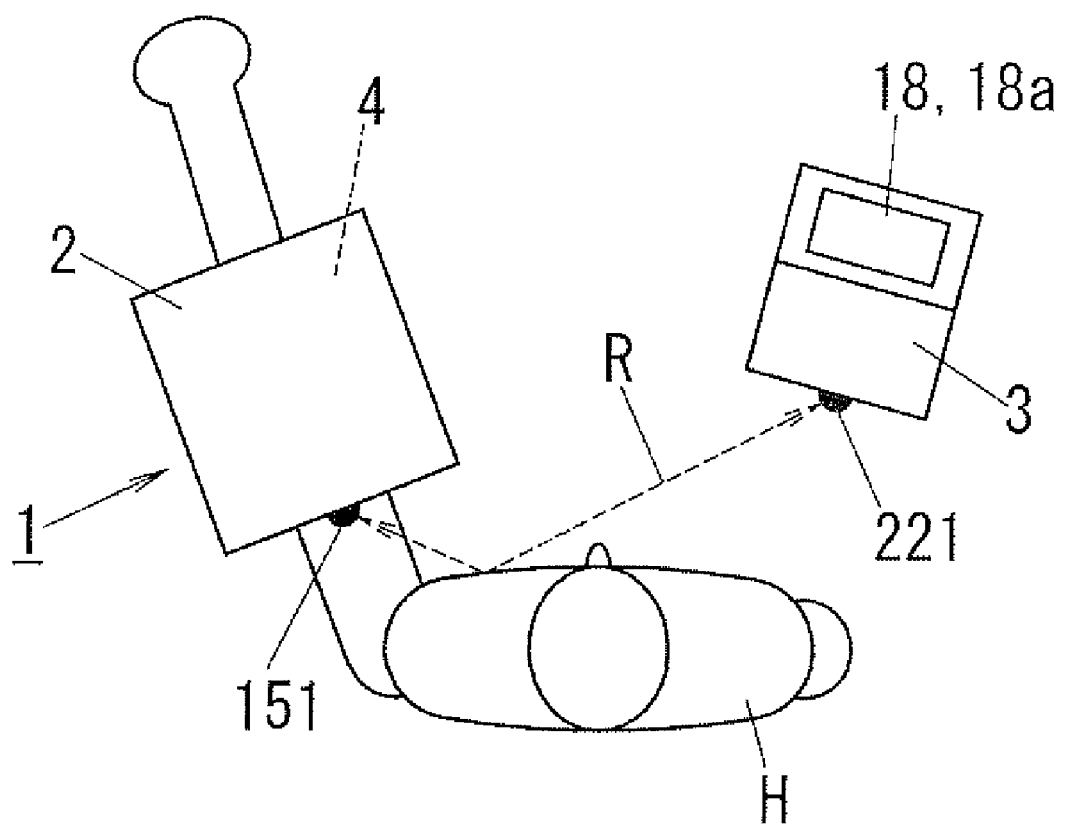
FIG. 1 is a schematic diagram of a blood pressure manometer in accordance with an embodiment of the present invention.
Figure 2:
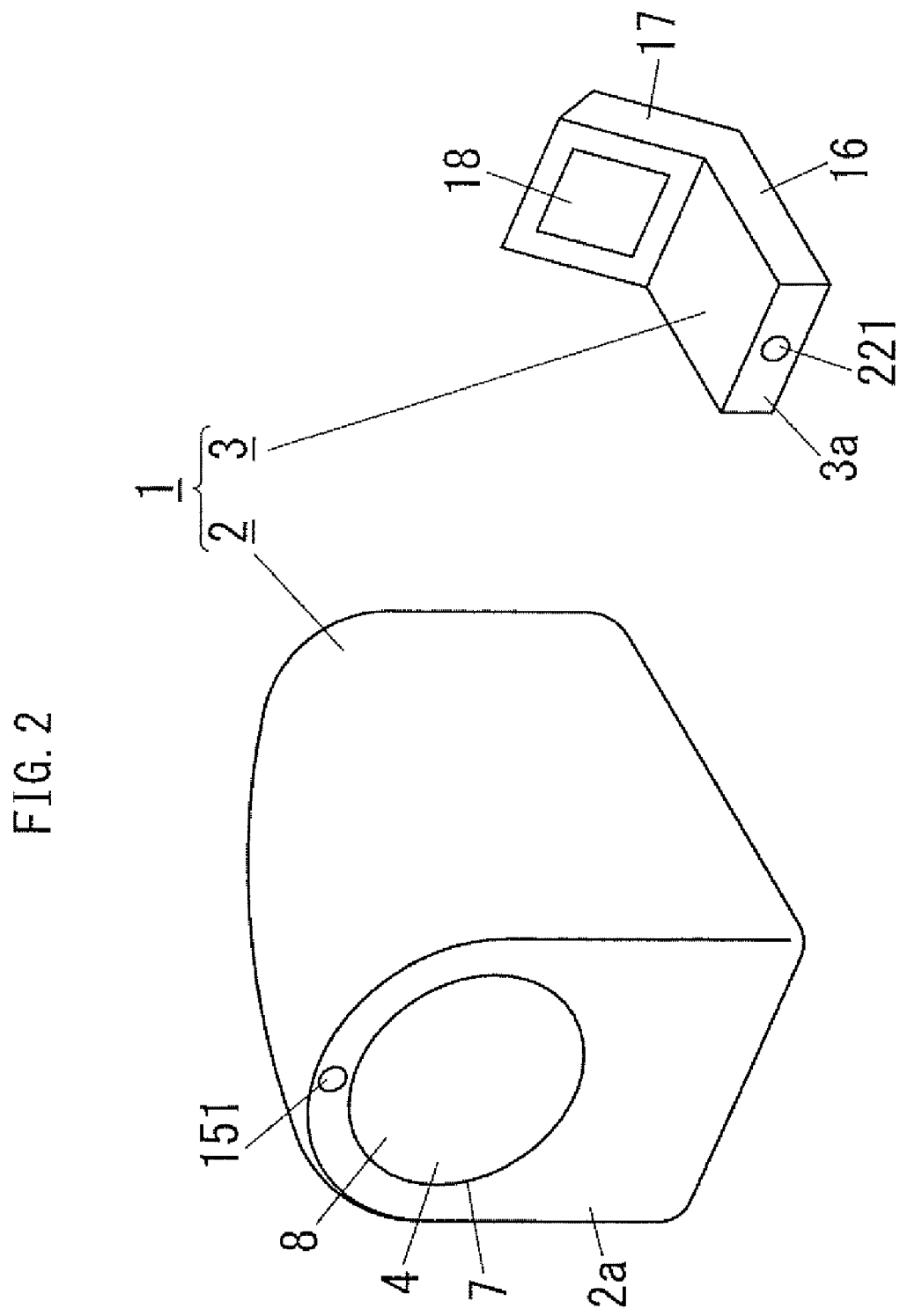
FIG. 2 is a perspective view of the blood pressure manometer.
Figure 3:
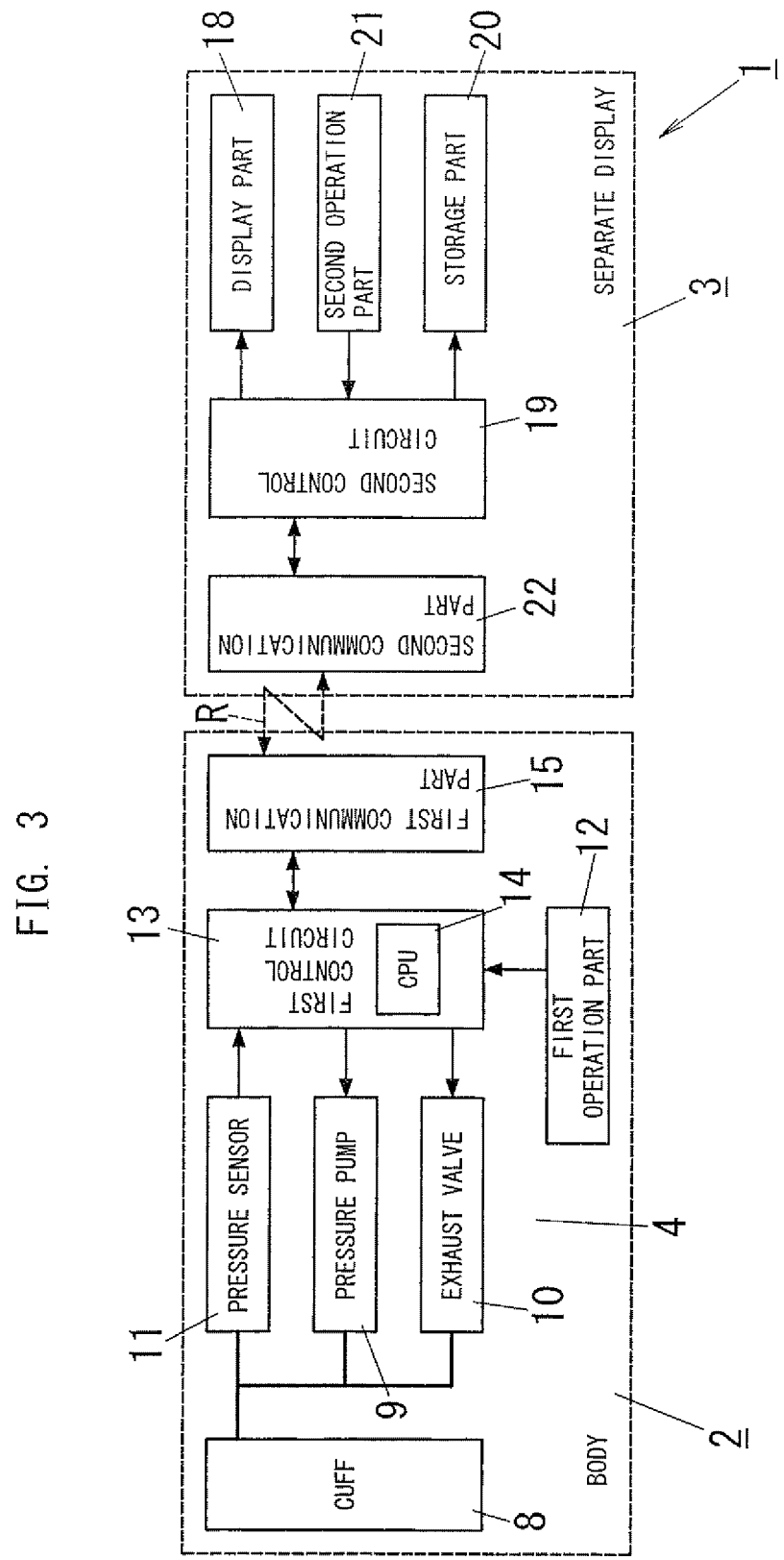
FIG. 3 is a block diagram of the blood pressure manometer.

As shown in FIGS. 1-3, a blood pressure manometer 1 in accordance with an embodiment of the present invention comprises a body 2 and a separate display 3. The body 2 includes a blood pressure measuring portion 4 that is configured to measure blood pressure of a subject (H) from either of the subject's left and right arms to obtain blood pressure data. The separate display 3 is separated from the body 2. The body 2 and separate display 3 are also provided with wireless infrared communication type of first and second communication parts 15 and 22, respectively. The separate display 3 is further provided with a display part 18 for displaying the subject's blood pressure based on the blood pressure data (e.g., blood pressure values, etc.) obtained through the communication parts 15 and 22. In FIGS. 1 and 3, R depicts an infrared signal.

The body 2 is formed for and backward with an insertion hole (through hole) 7 into which an arm of the subject (H) can be inserted. The blood pressure measuring portion 4 is provided with a cuff 8 that is configured to expand so as to press an arm of the subject (H) to then shrink and is located in the insertion hole 7. The cuff 8 expands by air supplied from a pressure pump 9, and then the air in the cuff 8 is exhausted through an exhaust valve 10. The body 2 is further provided with a pressure sensor 11, a first operation part 12 and a first control circuit 13. The pressure sensor 11 is used to detect a pressure value in the cuff 8 expanded and shrunk. The first operation part 12 is configured to provide the first control circuit 13 with an instruction of blood pressure measuring operation obtained by being handled by the subject (H). The first control circuit 13 is connected with the pressure sensor 11, the first operation part 12 and so on, and is configured to perform operation control of the body 2 such as operation control of the pressure pump 9 and exhaust valve 10, etc. The first control circuit 13 includes a CPU 14 that takes measurement data measured by the measuring portion 4 and then performs a calculating process to work out blood pressure values (blood pressure data). In addition, the first control circuit 13 is connected with the above-mentioned first communication part 15.

The separate display 3 is in the shape of a bent panel. That is, the front and rear halves of the separate display 3 can be classified into a horizontal panel part 16 and a slope panel part 17 sloping diagonally upwards, respectively. Said display part 18 is located on the front surface of the slope panel part 17. The display on the display part 18 is controlled through a second control circuit 19 for performing operation control of the separate display 3. The separate display 3 is provided with a storage part 20 for storing said blood pressure data, a second operation part 21 used to operate display contents on the display part 18 or the like, and said second communication part 22, besides the display part 18 and the second control circuit 19. The storage part 20, second operation part 21 and second communication part 22 are connected with the second control circuit 19.

The first communication part 15 has a light emitting element 151, and is configured so that the light emitting element 151 sends an infrared signal including the blood pressure data. The second communication part 22 has a light receiving element 221, and is configured so that the light receiving element 221 receives the infrared signal including the blood pressure data from the first communication part 15. However, not limited to these, the second communication part 22 may further comprise a light emitting element and send an infrared signal including an instruction and so on, and also the first communication part 15 may further comprise a light receiving element and receive the infrared signal including the instruction and so on.

As shown in FIG. 1, the blood pressure manometer 1 measures blood pressure of a subject (H) in the state that the subject inserts the arm extended forward into the insertion hole 7. In this case, the separate display 3 is located in front of the subject so that the subject can easily see the display part 18. Specifically, either of the subject's left and right arms is inserted into the insertion hole 7 but even if the subject inserts any arm into the insertion hole 7, the subject comes to exist in front of and near the body 2. Thus, the front of the body 2 and the front of the separate display 3 come to face the subject (H) in all arms.

Herein, the light emitting element 151 of the first communication part 15 is located at the upper part of the front 2a of the body 2, and the light receiving element 221 of the second communication part 22 is located at the center of the front side 3a of the separate display 3. That is, the subject (H) exists in an output angle range of an infrared signal from the light emitting element 151, and also exists in an input angle range of an infrared signal into the light receiving element 221. Therefore, an infrared signal (R) sent from the light emitting element 151 is reflected on the subject (H), and the reflected infrared signal (R) is received by the light receiving element 221. Similarly, in case of two-way infrared communication, an infrared signal sent from the light emitting element of the second communication part 22 is reflected on the subject, and the reflected infrared signal is received by the light receiving element of the first communication part 15.

In the embodiment, when the blood pressure manometer 1 measures blood pressure of a subject (H) from either of the subject's left and right arms, the subject (H) exists in front of and near the body 2 and the separate display 3. Especially, the front of the body 2 and the front of the separate display 3 face the subject's body such as breast, abdomen and so on. Therefore, existence of an obstacle(s) between the subject and the blood pressure manometer 1 can be eliminated. Moreover, in order to make the infrared signal from the first communication part 15 to the second communication part 22 reflect on the subject, the first and second communication parts do not need to be provided with a plural of light emitting elements and a plural of light receiving elements, respectively. Accordingly, it is possible to avoid an increase in the number of elements of the first and second communication parts to realize downsizing and cost reduction, without restricting working conditions while making it possible to measure the subject's blood pressure from any of the subject's left and right arms.

Figure 4:
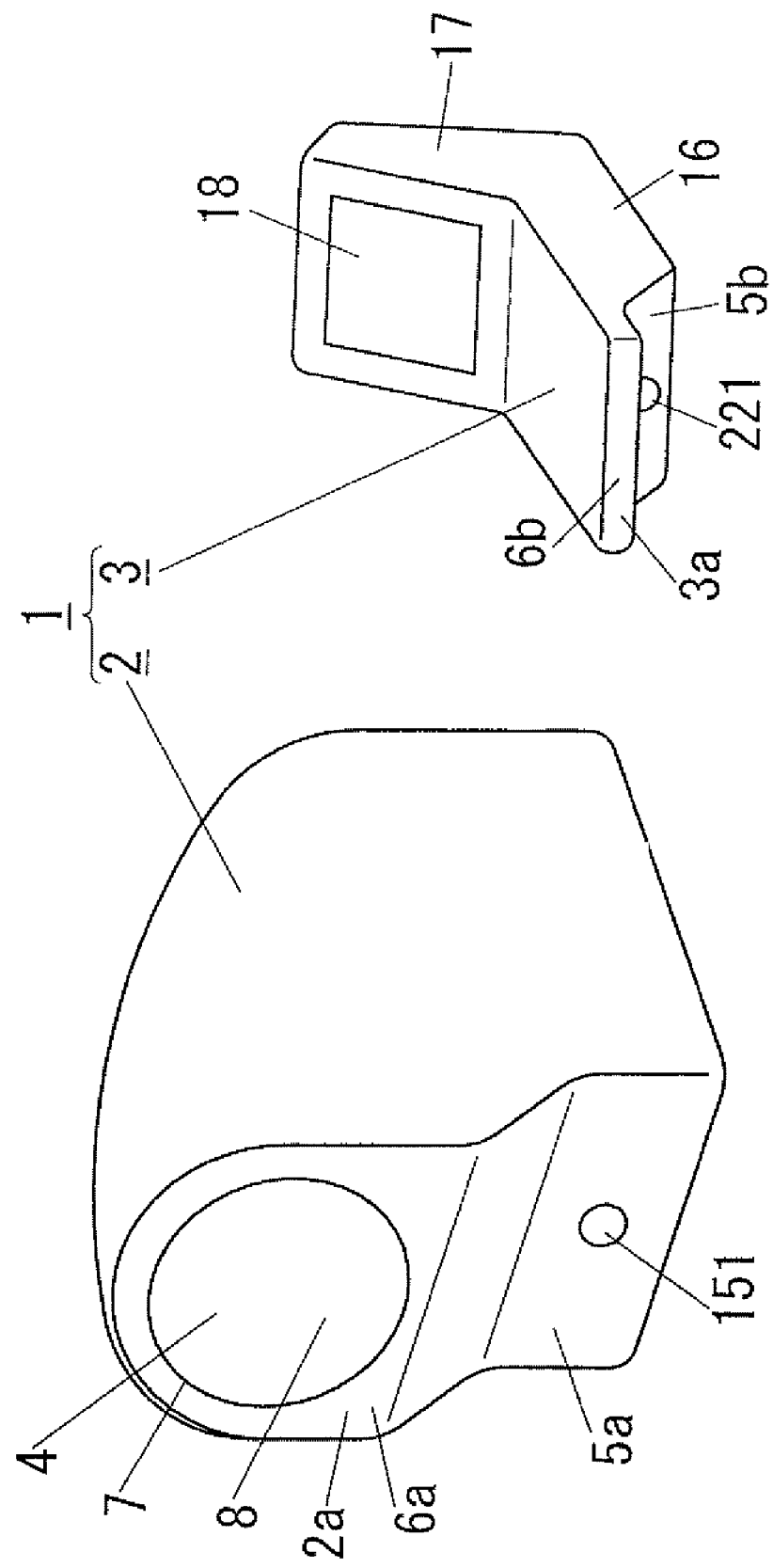
FIG. 4 is a perspective view of a blood pressure manometer in accordance with an embodiment of the present invention.
Figure 5:
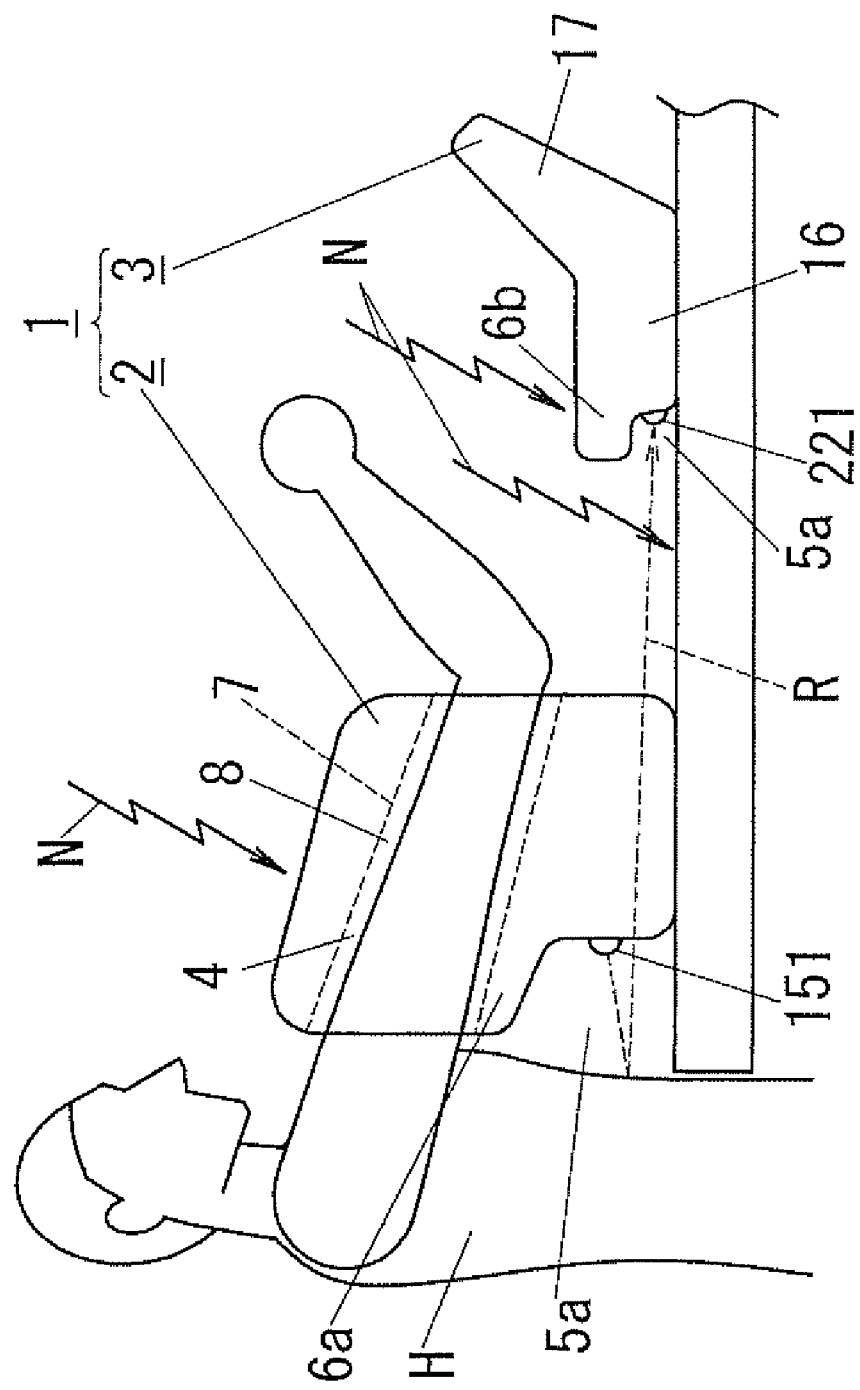
FIG. 5 is an explanatory diagram of operation of the blood pressure manometer.

In an embodiment, as shown in FIGS. 4 and 5, the front 2a of the body 2 is formed with a protuberance 6a and a recess 5a arranged up and down, respectively. The protuberance 6a includes the cuff 8, and the recess 5a is provided with the light emitting element 151. In addition, the front side 3a of the separate display 3 is formed with an eaves 6b and a recess 5b arranged up and down, respectively. The recess 5b is provided with the light receiving element 221. The light emitting element 151 and light receiving element 221 can be seen from the left and right sides but cannot be seen from the upper side due to the protuberance 6a and eaves 6b. In this embodiment, it is possible to prevent the subject from covering the light emitting element 151 and light receiving element 221 by mistake. Consequently, the interruption of infrared communication pass between the elements can be avoided. Moreover, the protuberance 6a and eaves 6b (especially 6b) can block noise (N) from fluorescent lamps to the light emitting element 151 and light receiving element 221 (especially 221), and accordingly malfunction of the blood pressure manometer 1 by the noise can be prevented. In an example, the body 2 may comprise eaves at left, right and/or bottom of the recess 5a, and the separate display 3 may also comprises eaves at left, right and/or bottom of under the recess 5b.

Figure 6:
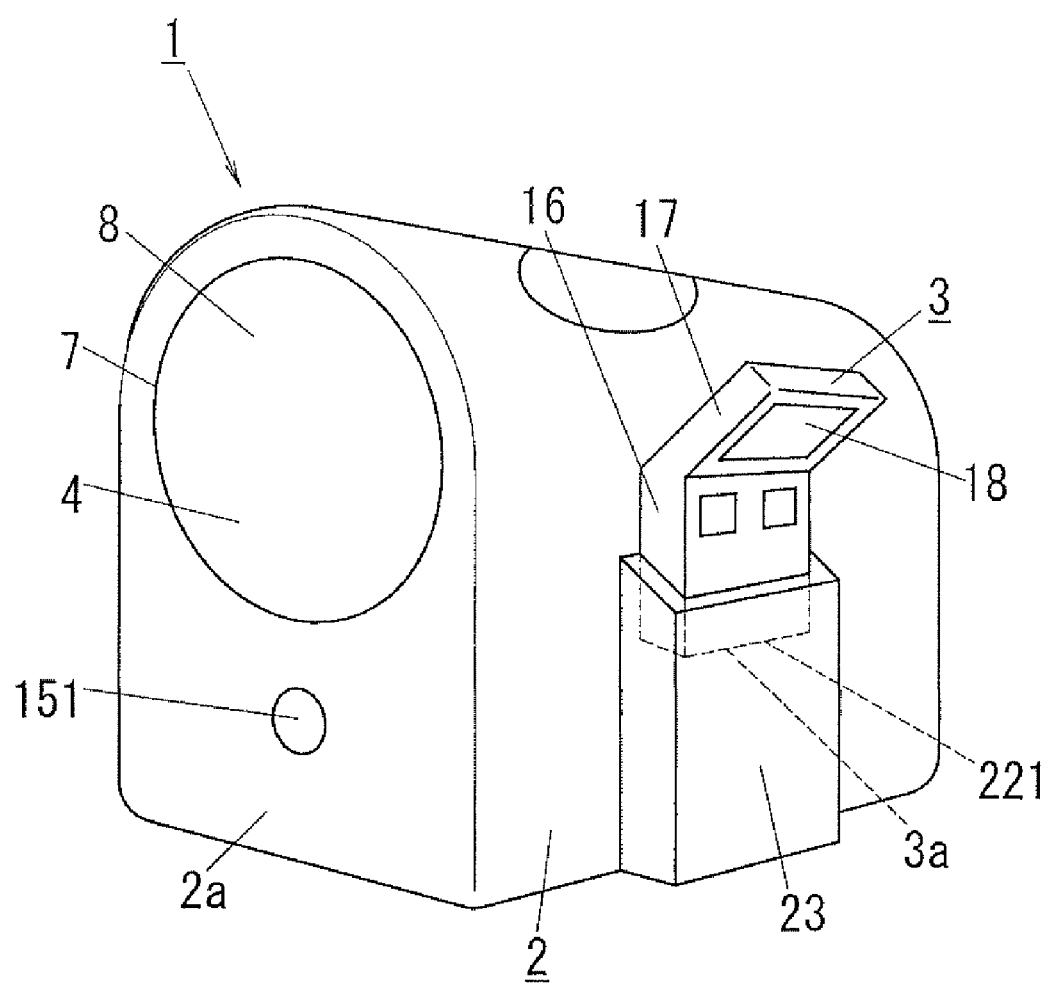
FIG. 6 is a perspective view of a blood pressure manometer in accordance with an embodiment of the present invention.

In an embodiment, as shown in FIGS. 6, 7A and 7B, the separate display 3 can be attached to and detached from the body 2. In addition, the body 2 further comprises an interruption means which interrupts the communication pass between the first and second communication parts 15 and 22 when the separate display 3 is attached to the body 2.

In an example of FIG. 6, a pocket shaped holder 23 opening upward is formed on one of the left and right sides (e.g., right side) of the body 2. If the horizontal panel part 16 of the separate display 3 is inserted into the holder 23, the separate display 3 is held by the body 2. In this case, since the light receiving elements 221 of the separate display 3 is covered with the holder 23, the communication pass between the first and second communication parts 15 and 22 is interrupted. That is, the interruption means of FIG. 6 is formed of the holder 23.

In an example of FIGS. 7A and 7B, the front opening of the insertion hole 7 is used as a holder 23b. If the corners of projection part in the horizontal panel part 16 and slope panel part 17 are fit into the holder 23b, the separate display 3 is held by the body 2. In this case, the body 2 is mounted with the separate display 3 so as to close the front opening of the insertion hole 7, and the light receiving element 221 of the separate display 3 is put in the insertion hole 7 to face the inner face of the hole 7. In short, the light receiving element 221 is covered with the holder 23b and the communication pass between the first and second communication parts 15 and 22 is interrupted, and accordingly the interruption means of FIGS. 7A and 7B is formed of the holder 23b.

In the embodiment of FIGS. 6, 7A and 7B, when the separate display 3 is attached to the body 2, namely when the blood pressure manometer 1 is not used, it is possible to prevent malfunction of the manometer 1 by unwanted communication between the first and second communication parts.

The blood pressure manometer 1 of FIGS. 7A and 7B is supplemented. The body 2 is formed of a base 24 and the blood pressure measuring portion 4. The base 24 can be put on a mount surface, such as on a desk or the like. The blood pressure measuring portion 4 is in the shape of a cylinder, and is pivoted on a shaft 24a of the base 24 so that the axis of the portion 4 can be moved horizontally when it is used and moved vertically when it is not used. The light emitting element 151 is located at the front end side of the base 24 in the cylindrical surface of the blood pressure measuring portion 4, and sends an infrared signal diagonally forward when the blood pressure manometer 1 is used. In case of two-way infrared communication, the blood pressure measuring portion 4 can block noise from fluorescent lamps to the light receiving element located near the light emitting element 151.

In an embodiment, as shown in FIGS. 8A, 8B, 9A, 9B and 9C, the separate display 3 can be attached to and detached from the body 2, and the first and/or second communication part is configured to turn off (stop function of itself) when the separate display 3 is attached to the body 2.

Figure 8A:
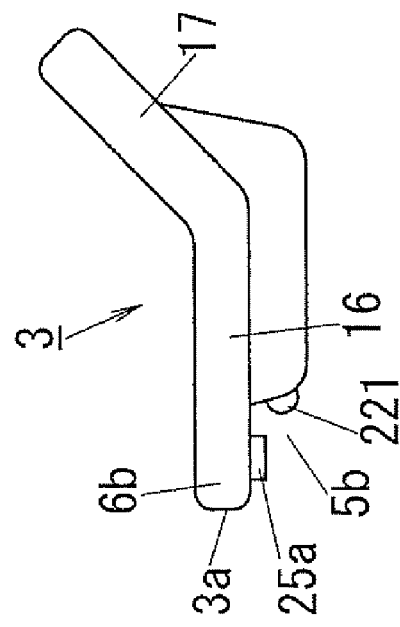
FIG. 8A is a lateral view of a separate display in a blood pressure manometer in accordance with an embodiment of the present invention.
Figure 8B:
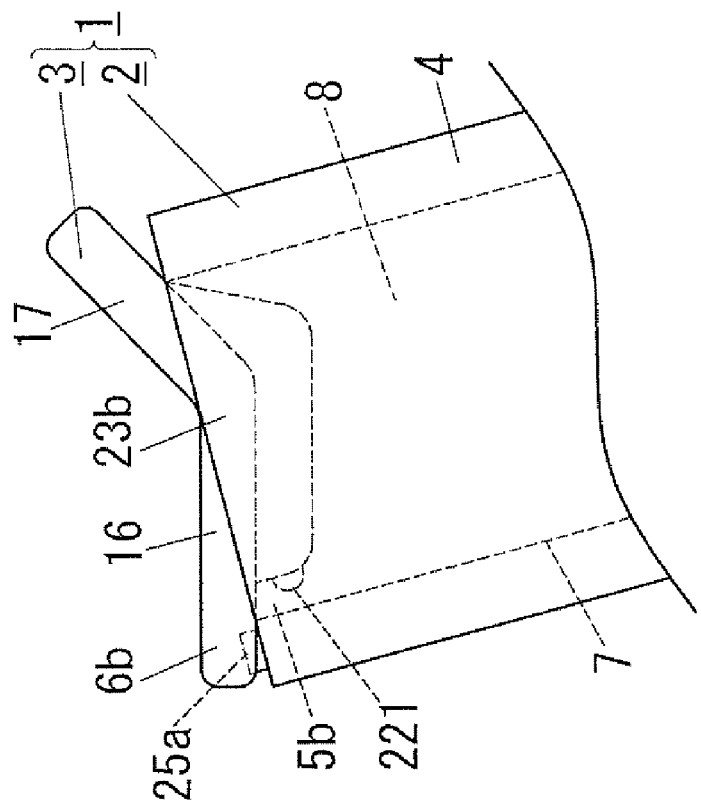
FIG. 8B is a lateral view of the essential parts of the blood pressure manometer when it is not used.

In an example of FIGS. 8A and 8B, the separate display 3 comprises a power switch 25a, and the switch 25a is located at the bottom of the eaves 6b. When the holder 23b of the body 2 is mounted with the separate display 3, the power switch 25a is pressed with the front edge of the insertion hole 7 and then a power source of the separate display 3 is turned off. Consequently, the second communication part 22 stops the function. When the separate display 3 is detached from the body 2, the power switch 25a is turned on and then the power source of the separate display 3 is turned on. Therefore, the second communication part 22 is turned on.

Figure 9A:
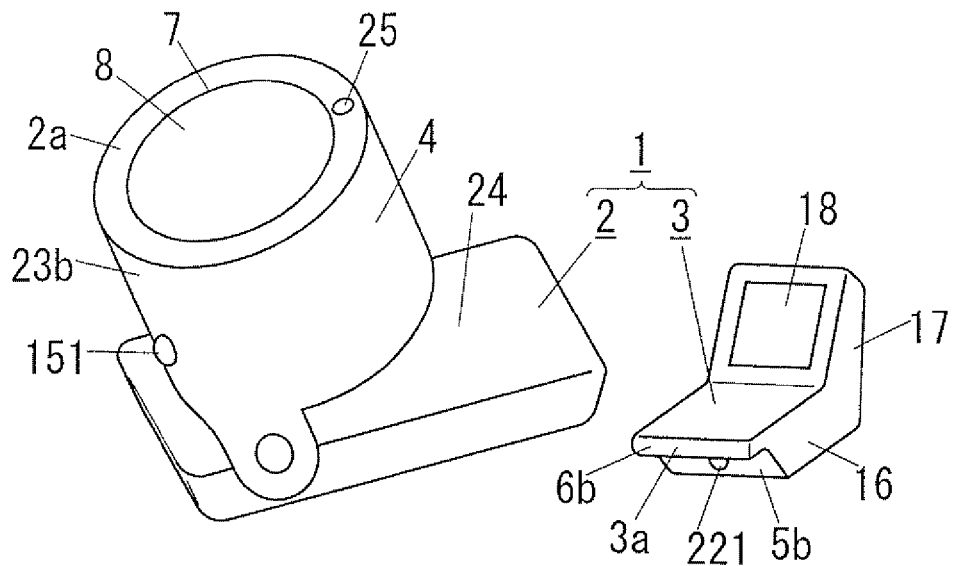
FIG. 9A is a schematic diagram of a blood pressure manometer in accordance with an embodiment of the present invention.
Figure 9B:
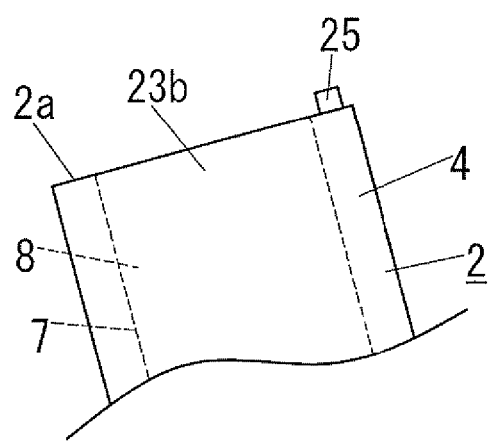
FIG. 9B is a lateral view of the essential parts of the blood pressure manometer when it is used.
Figure 9C:
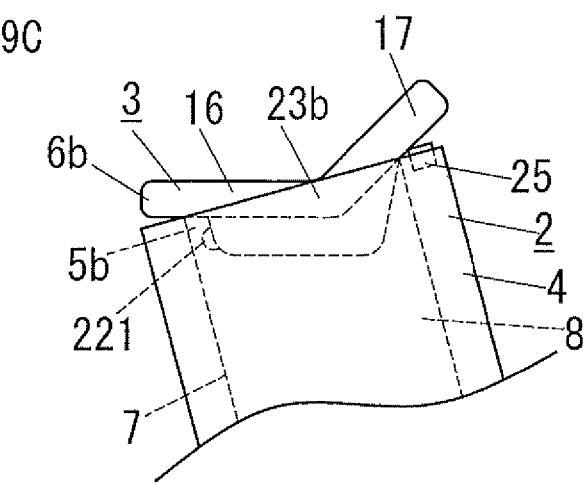
FIG. 9C is a lateral view of the essential parts of the blood pressure manometer when it is not used.

In an example of FIGS. 9A, 9B and 9C, the body 2 comprises a power switch 25b, and the switch 25b is located at the front edge of the insertion hole 7. When the holder 23b of the body 2 is mounted with the separate display 3, the power switch 25b is pressed with the rear of the separate display 3 and then a power source of the body 2 is turned off. Consequently, the first communication part 15 stops the function. When the separate display 3 is detached from the body 2, the power switch 25b is turned on and then the power source of the body 2 is turned on. Therefore, the first communication part 15 is turned on.

In the embodiment of FIGS. 8A, 8B, 9A, 9B and 9C, when the holder 23b of the body 2 is mounted with the separate display 3, it is possible to prevent malfunction of the blood pressure manometer 1 by unwanted communication between the first and second communication parts. Moreover, a power source of the body 2 or separate display 3 is turned off and thereby power saving can be achieved.

Figure 10:
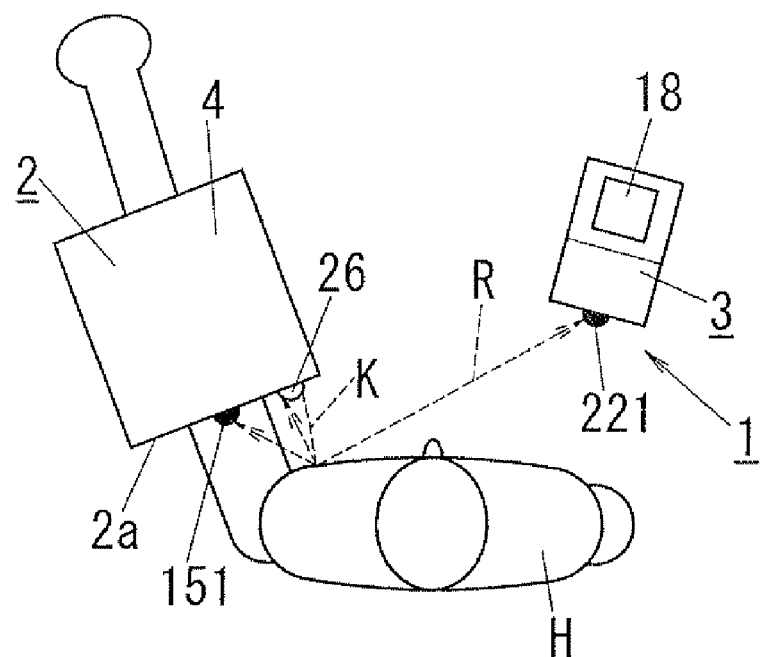
FIG. 10 is an explanatory diagram of operation of a blood pressure manometer in accordance with an embodiment of the present invention.
Figure 11:
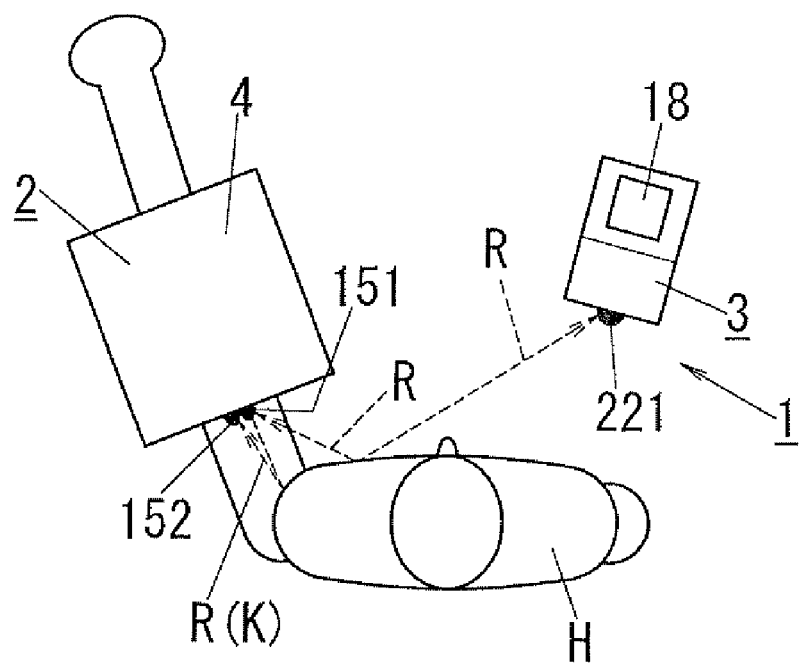
FIG. 11 is an explanatory diagram of operation of a blood pressure manometer in accordance with an embodiment of the present invention.

In an embodiment, as shown in FIGS. 10 and 11, the body 2 comprises a human body sensor configured to detect whether or not a human body exists in a target space. In addition, the first control circuit 13 is configured to stop operation of the blood pressure measuring portion 4 when the human body sensor detects that a human body does not exist in the target space.

In an example of FIG. 10, the body 2 comprises a human body sensor 26 configured to detect whether or not a human body exists in a predetermined target space. The human body sensor 26 is connected with the first control circuit 13. The first control circuit 13 is configured to stop operation of the blood pressure measuring portion 4 when the human body sensor 26 detects that a human body does not exist in the target space. When blood pressure is measured, a subject (H) exists in front of the body 2 and therefore the human body sensor 26 is located at the front 2a of the body 2. The human body sensor 26 can be formed of, for example, a transmitter and a receiver. The transmitter sends a sensing signal such as a microwave, infrared or the like, and the receiver receives the sensing signal that is sent from the transmitter and then reflected on the subject (H).

In an example of FIG. 11, the body 2 comprises a human body sensor formed of the light emitting element 151 and a light receiving element 152. The light emitting element 152 is connected with the first control circuit 13. The first control circuit 13 sends an infrared signal through the light emitting element 151 when detecting a human body. At this point, if receiving the infrared signal through the light receiving element 152, the first control circuit 13 detects that a human body exists in a predetermined target space. The first control circuit 13 otherwise detects that a human body does not exist in the target space. When detecting that a human body does not exist in the target space, the first control circuit 13 stops operation of the blood pressure measuring portion 4.

In the embodiment of FIGS. 10 and 11, it is possible to prevent unwanted operation of the blood pressure measuring portion 4 when a subject does not exist in the target space.

In an embodiment, as shown in FIGS. 12A, 12B, 13A, 13B, 14A and 14B, the separate display 3 further comprises a notice means configured to notify the subject (H) of strength of the infrared signal received by the light receiving element 221. In case of two-way infrared communication, the body 2 may also comprise a notice means formed similarly.

In an example of FIGS. 12A, 12B, 13A and 13B, the notice means is formed of the display part 18 and the second control circuit 19. The display part 18 is, for example, an LCD (liquid crystal display). The second control circuit 19 has thresholds (e.g., three thresholds), and changes an image (icon) displayed on the display part 18 in response to strength of the infrared signal received by the light receiving element 221. For example, in response to strength of the infrared signal, the second control circuit 19 changes the number of bars 27 in the image into 0, 1, 2 or 3. The number of bars 27 in the image 18a of FIG. 12B is 3, and the strength of the infrared signal is strongest. The number of bars 27 in the image 18b of FIG.

13B is zero, and this image 18b represents that infrared communication between the first and second communication parts is impossible.

Figure 14A:
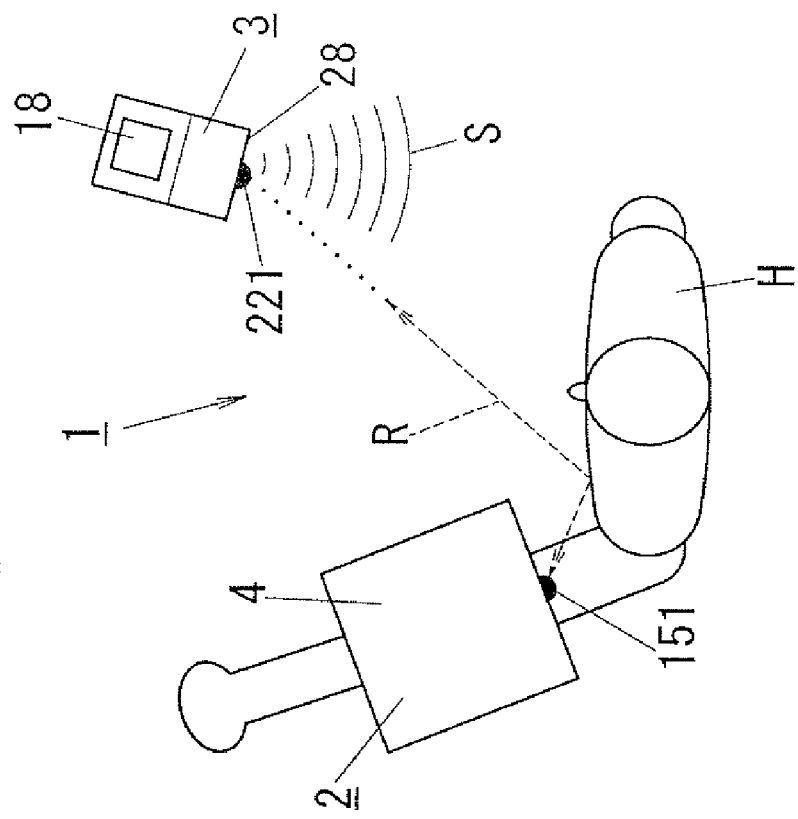
FIG. 14A is an explanatory diagram of operation in case of good infrared communication of a blood pressure manometer in accordance with an embodiment of the present invention.
Figure 14B:
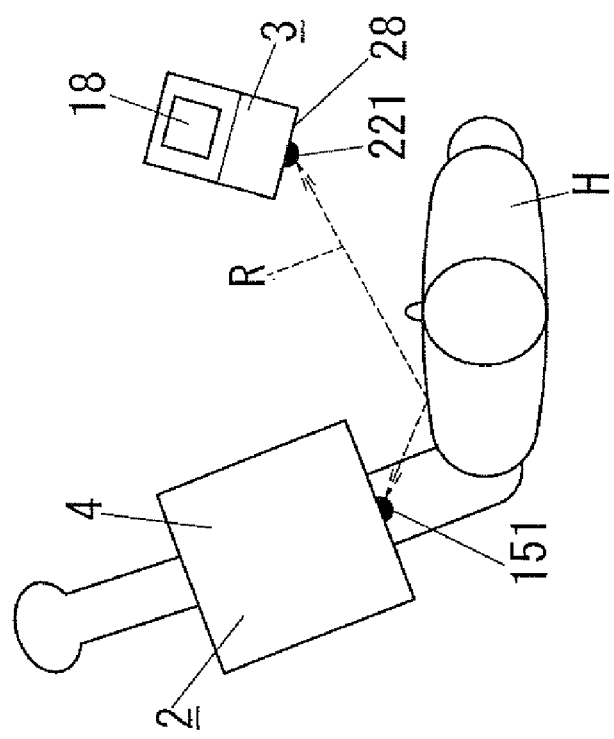
FIG. 14B is an explanatory diagram of operation in case of no good infrared communication of the blood pressure manometer.
Figure 15B:
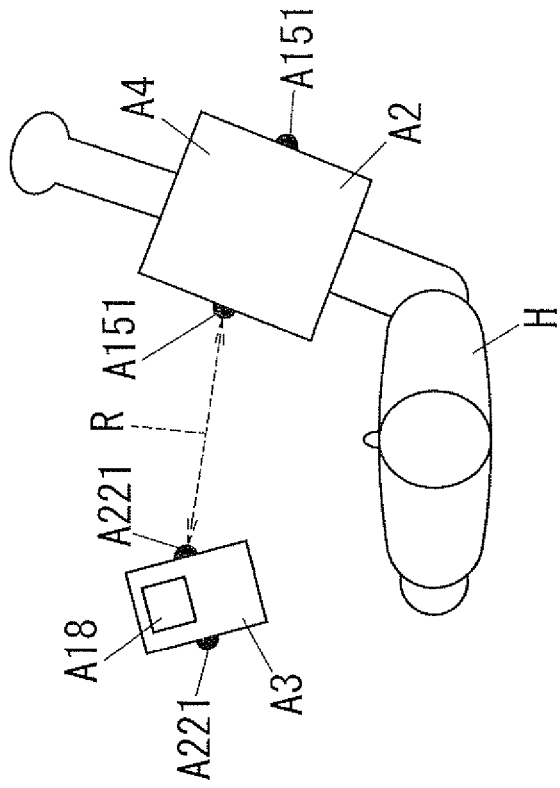
FIGS. 15A and 15B illustrate an improvement example of a prior art.
Figure 15A:
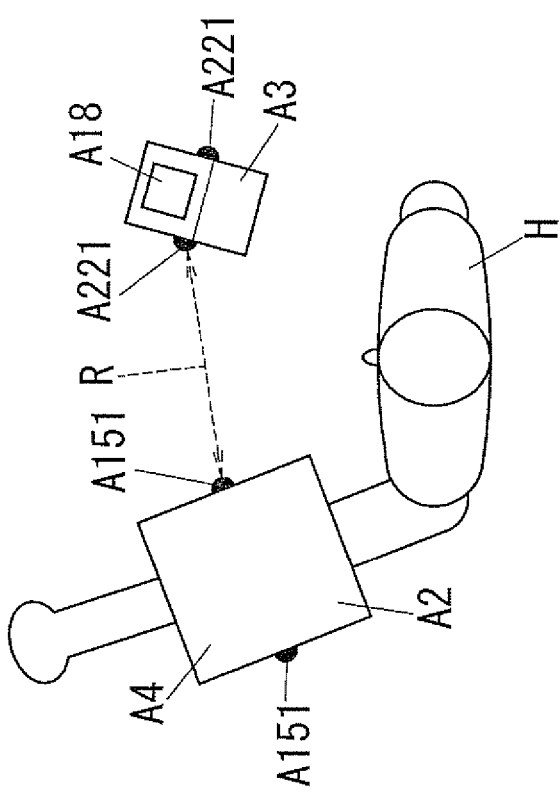

In an example of FIGS. 14A and 14B, the notice means is formed of a speaker 28 and the second control circuit 19. When strength of the infrared signal received by the light receiving element 221 is weaker than a predetermined strength, the second control circuit 19 judges that infrared communication between the first and second communication parts is impossible or no good, and then drives the speaker 28. At this point, the second control circuit 19 gives an alarm, for example, such as "Pi, Pi, Pi, . . . " through the speaker 28. However, not limited to this, the second control circuit 19 may give voice announcement through the speaker 28.

In the embodiment of FIGS. 12A, 12B, 13A, 13B, 14A and 14B, the separate display 3 can be prevented from being moved too far from the body 2, and good infrared communication between the first and second communication parts can be secured. Consequently, a measurement error can be avoided. Loss of the separate display 3 can be also prevented. In an example, the second operation part 21 may comprise a button for turning on and off the notice means. Similarly, in case of two-way infrared communication, the first operation part 12 may comprise a button for turning on and off the notice means of the body 2. In these cases, when the separate 3 will be shown to a doctor, the notice means of the separate display 3 (or body 2) can be turned off, and such button is effective in especially the notice means of FIGS. 14A and 14B.

In an embodiment, the slope panel part 17 of the separate display 3 can be tilted and reclined with respect to the horizontal panel part 16.

Although the present invention has been described with reference to certain preferred embodiments, numerous modifications and variations can be made by those skilled in the art without departing from the true spirit and scope of this invention.

The invention claimed is:

1. A blood pressure manometer, comprising:
a blood pressure measuring portion configured to measure a subject's blood pressure from either of the subject's left and right regions to obtain blood pressure data;
a first communication part having a light emitting element, the first communication part being configured so that the light emitting element sends an infrared signal including the blood pressure data;
a body comprising the blood pressure measuring portion and the first communication part;
a second communication part having a light receiving element, the second communication part being configured so that the light receiving element receives the infrared signal including the blood pressure data from the first communication part;
a display part configured to display the subject's blood pressure based on the blood pressure data included in the infrared signal received by the light receiving element; and
a separate display which is separated from the body and comprises the second communication part and the display part;
wherein: the light emitting element is supported by the body to be opposite the subject even if the blood pressure measuring portion measures the subject's blood pressure from any of the subject's left and right regions; and
the light receiving element is supported by the separate display to receive the infrared signal which is sent from the light emitting element to be reflected on a main body portion of the subject, the main body portion comprising a breast and an abdomen of the subject,
wherein the light emitting element is located at a front side of the body that is opposite the subject, and the light receiving element is located at a front side of the separate display that is opposite the subject when the display part is opposite the subject, and
wherein the light emitting element directs the infrared signal towards the subject to be reflected off of the subject.

2. The blood pressure manometer of claim 1, wherein:
the blood pressure measuring portion includes a cuff into which either of the subject's left and right arms is inserted and is configured to measure the subject's blood pressure through the cuff to obtain blood pressure data.

3. The blood pressure manometer of claim 2, wherein:
the front of the body is formed with a protuberance and a recess arranged up and down, respectively, the protuberance including the cuff, the recess including the light emitting element; and
the front side of the separate display is formed with an eaves and a recess arranged up and down, respectively, the recess including the light receiving element.

4. The blood pressure manometer of claim 2, wherein:
the separate display is configured to be either attached to or detached from the body; and
the body further comprises an interruption means which interrupts the communication pass between the first and second communication parts when the separate display is attached to the body.

5. The blood pressure manometer of claim 2, wherein:
the separate display is configured to be either attached to or detached from the body; and
the body further comprises a switch, the switch turning on at least the first communication part when the separate display is detached from the body, the switch also turning off at least the first communication part when the separate display is attached to the body.

6. The blood pressure manometer of claim 2, wherein:
the separate display is configured to be either attached to or detached from the body; and
the separate display further comprises a switch, the switch turning on at least the second communication part when the separate display is detached from the body, the switch also turning off at least the second communication part when the separate display is attached to the body.

7. The blood pressure manometer of claim 5, wherein:
the separate display is configured to be either attached to or detached from the body; and
the separate display further comprises a switch, the switch turning on at least the second communication part when the separate display is detached from the body, the switch also turning off at least the second communication part when the separate display is attached to the body.

8. The blood pressure manometer of claim 2, wherein the body further comprises:
a human body sensor configured to detect whether or not a human body is present within a target space; and
a controller configured to stop operation of the blood pressure measuring portion when the human body sensor detects that a human body is not present within the target space.

9. The blood pressure manometer of claim 2, wherein the separate display further comprises a notice means configured to notify the subject of strength of the infrared signal received by the light receiving element.

10. The blood pressure manometer of claim 1,
wherein the blood pressure measuring portion includes a cuff which is configured so that either of the subject's left and right arms is inserted into the cuff, said blood pressure measuring portion being configured to measure a subject's blood pressure through the cuff to obtain blood pressure data,
wherein the body is formed forward and backward with an insertion hole configured to accept an arm of the subject into the insertion hole,
wherein the cuff is located in the insertion hole,
wherein the light emitting element is located at an upper or lower part of the front of the body, and thereby supported by the body to face the subject even if the blood pressure measuring portion measures the subject's blood pressure from any of the subject's left and right regions,
wherein the light receiving element is located at the center of the front side of the separate display to face the subject's breast or abdomen when the display part faces the subject, and thereby supported by the separate display to receive the infrared signal which is sent from the light emitting element to be reflected at the subject's breast or abdomen.

\* \* \* \* \*